(12) United States Patent
Lambert et al.

(10) Patent No.: US 9,915,606 B2
(45) Date of Patent: Mar. 13, 2018

(54) METHOD FOR TRANSFERRING BETWEEN SPECTROMETERS

(71) Applicant: Topnir Systems SAS, Aix-en-Provence (FR)

(72) Inventors: Didier Lambert, Bernos-Beaulac (FR); Claude Saint Martin, Pelissane (FR); Sanchez Miguel, Lavera (FR); Bernard Ribero, Marseilles (FR)

(73) Assignee: Topnir Systems SAS, Aix-en-Provence (FR)

( * ) Notice: Subject to any disclaimer, the term of this patent is extended or adjusted under 35 U.S.C. 154(b) by 0 days.

(21) Appl. No.: 14/904,634

(22) PCT Filed: Jul. 10, 2014

(86) PCT No.: PCT/EP2014/064808
§ 371 (c)(1),
(2) Date: Jan. 12, 2016

(87) PCT Pub. No.: WO2015/004234
PCT Pub. Date: Jan. 15, 2015

(65) Prior Publication Data
US 2016/0153899 A1   Jun. 2, 2016

(30) Foreign Application Priority Data
Jul. 12, 2013   (EP) .................................... 13290161

(51) Int. Cl.
*G01J 5/02*   (2006.01)
*G01N 21/359*   (2014.01)
(Continued)

(52) U.S. Cl.
CPC ......... *G01N 21/359* (2013.01); *G01N 21/274* (2013.01); *G01N 21/35* (2013.01); *G01N 2201/127* (2013.01)

(58) Field of Classification Search
CPC .......................... G01N 21/278; G01N 21/274
(Continued)

(56) References Cited

U.S. PATENT DOCUMENTS

2005/0119541 A1   6/2005   Lorenz et al.
2007/0112258 A1   5/2007   Soyemi
(Continued)

FOREIGN PATENT DOCUMENTS

| | | |
|---|---|---|
| EP | 0742900 | 3/1999 |
| EP | 1726929 | 11/2006 |

(Continued)

OTHER PUBLICATIONS

Pereira et al. "A Comparative study of calibration transfer methods for determination of gasoline quality parameters in three different near infrared spectrometers" Analytica Chimica Acta, Elseveir, Amsterdam, NL, vol. 611, No. 1 Feb. 7, 2008.
(Continued)

*Primary Examiner* — Kenneth J Malkowski
(74) *Attorney, Agent, or Firm* — Gable Gotwals (57) ABSTRACT

The present invention relates to a method for characterizing a sample-product X by spectral analysis by means of a novel spectrometer II using information acquired by means of a first spectrometer I.

3 Claims, 4 Drawing Sheets

(51) Int. Cl.
*G01N 21/27* (2006.01)
*G01N 21/35* (2014.01)

(58) Field of Classification Search
USPC .................................................. 250/252.1
See application file for complete search history.

(56) References Cited

U.S. PATENT DOCUMENTS

| 2007/0188751 | A1* | 8/2007 | Kawano | G01J 3/28 |
| | | | | 356/319 |
| 2009/0112475 | A1 | 4/2009 | Christy et al. | |

FOREIGN PATENT DOCUMENTS

| EP | 2799840 | 4/2013 |
| EP | 2799841 | 4/2013 |
| WO | 9632631 | 10/1996 |
| WO | 2006126978 | 11/2006 |

OTHER PUBLICATIONS

Elvira Fernandez-Ahumada et al. "Talking NIR Calibrations of Feed Compounds from the Laboratory to the Process: Calibration Transfer between Predispersive and Postdispersive Instruments", Journal of Agricultural and Food Chemistry, vol. 56, No. 21 Nov. 12, 2008.
M.Forina "Transfer of calibration function in near-infrared spectroscopy" Chemometrics and Intelligent Laboratory Systems, vol. 27, Issue 2, Feb. 1995.

* cited by examiner

| Absorbance | % Weight | Germ 1 | Germ 2 | Germ 3 | 4764 | 4760 | 4756 | 4752 | 4748 | 4744 | 4740 | 4736 | 4732 | Mon | Ron |
|---|---|---|---|---|---|---|---|---|---|---|---|---|---|---|---|
| A0000001 | | | | | 7.78E-06 | 1.29E-05 | 1.88E-05 | 2.42E-05 | 3.16E-05 | 4.42E-05 | 6.18E-05 | 8.01E-05 | 9.88 E-05 | 85.1 | 94.2 |
| A0000002 | | | | | 8.08E-06 | 1.37E-05 | 1.96E-05 | 2.5E-05 | 30.18E-05 | 4.46 E-05 | 6.09 E-05 | 7.91 E-05 | 9.8 E-05 | 85.3 | 94.7 |
| A0000003 | | | | | 8.78E-06 | 1.52E-05 | 2.23E-05 | 2.97E-05 | 3.99E-05 | 5.53 E-05 | 7.54 E-05 | 9.68 E-05 | 0.000118 | 85 | 94 |
| A0000004 | | | | | 7.46E-06 | 1.26E-05 | 1.81E-05 | 2.47E-05 | 3.29E-05 | 4.71 E-05 | 6.55 E-05 | 8.47 E-05 | 0.000104 | 85 | 93.5 |
| A0000005 | | | | | 1.01E-05 | 1.59E-05 | 2.39E-05 | 3.28E-05 | 4.34E-05 | 5.93 E-05 | 8.08 E-05 | 0.000104 | 0.000128 | 85.3 | 95.1 |
| A0000006 | | | | | 5.49E-06 | 9.2E-06 | 1.41E-05 | 1.88E-05 | 2.54E-05 | 3.62E-05 | 5.18E-05 | 6.97 E-05 | 8.68 E-05 | 84.4 | 92.8 |
| A0000007 | | | | | 7.14E-06 | 1.21E-05 | 1.86E-05 | 2.41E-05 | 3.27E-05 | 4.63E-05 | 6.52E-05 | 8.49 E-05 | 0.000104 | 85 | 93.5 |
| A0000008 | | | | | 1.03E-05 | 1.64E-05 | 2.4E-05 | 3.26E-05 | 4.39E-05 | 6.13E-05 | 8.42E-05 | 0.000109 | 0.000136 | 85.5 | 95.1 |
| A0000009 | | | | | 8.25E-06 | 1.15E-05 | 1.4E-05 | 1.62E-05 | 1.99E-05 | 2.56E-05 | 3.56E-05 | 4.94E-05 | 6.62E-05 | 85.4 | 95 |
| 12G022 | 0.564 0.436 | A0000003 | A0000006 | | 7.35E-06 | 1.26E-05 | 1.88E-05 | 2.49E-05 | 3.36E-05 | 4.7E-05 | 6.51E-05 | 8.5E-05 | 0.000105 | 84.73846 | 93.47693 |
| 12G011 | 0.654 0.346 | A0000009 | A0000001 | | 8.09E-06 | 1.2E-05 | 1.57E-05 | 1.9E-05 | 2.4E-05 | 3.2 E-05 | 4.47E-05 | 6E-05 | 7.75E-05 | 85.29608 | 94.72287 |
| 12G036 | 0.44 0.56 | A0000008 | A0000004 | | 8.69E-06 | 1.43E-05 | 2.07E-05 | 2.81E-05 | 3.77E-05 | 5.33E-05 | 7.38E-05 | 9.54E-05 | 0.000118 | 85.21994 | 94.20381 |
| 13G038 | 0.747 0.258 -0.005 | A0000008 | A0000002 | A0000004 | 9.71E-06 | 1.57E-05 | 2.29E-05 | 3.06E-05 | 4.09E-05 | 5.7E-05 | 7.83E-05 | 0.000101 | 0.000126 | 85.45096 | 95.00502 |
| 13G025 | 0.5825 0.3020 0.1155 | A0000008 | A0000005 | A0000003 | 1E-05 | 1.61E-05 | 2.38E-05 | 3.23E-05 | 4.33E-05 | 6 E-05 | 8.22E-05 | 0.000106 | 0.000131 | 85.38181 | 94.97284 |
| 13G019 | 0.094 -0.00047 0.00647 | A0000004 | A0000005 | A0000007 | 7.43E-06 | 1.25E-05 | 1.81E-05 | 2.46E-05 | 3.28E-05 | 4.7E-05 | 6.54E-05 | 8.46E-05 | 0.000104 | 84.99859 | 93.49245 |

EXTENDED SPECTRUM DATABASE WITH CHARACTERIZATION

| Spectra | Spectra $S_x^{II}$ | Spectra $S_x^{I}$ |
|---|---|---|
| | $\lambda_1, \lambda_2, \lambda_3, ...., \lambda_n$ | $\mu_1, \mu_2, \mu_3, ...., \mu_n$ |
| | | |
| Spectra $I_1$ | $VGS_{I1 \lambda1}^{II}, VGS_{I1 \lambda2}^{II}, ..., VGS_{I1 \lambda n}^{II}$ | $VGS_{I1 \mu1}^{I}, VGS_{I1 \mu2}^{I}, ..., VGS_{I1 \mu n}^{I}$ |
| Spectra $I_2$ | $VGS_{I2 \lambda1}^{II}, VGS_{I2 \lambda2}^{II}, ..., VGS_{I2 \lambda n}^{II}$ | $VGS_{I2 \mu1}^{I}, VGS_{I2 \mu2}^{I}, ..., VGS_{I2 \mu n}^{I}$ |
| Spectra $I_3$ | $VGS_{I3 \lambda1}^{II}, VGS_{I3 \lambda2}^{II}, ..., VGS_{I3 \lambda n}^{II}$ | $VGS_{I3 \mu1}^{I}, VGS_{I3 \mu2}^{I}, ..., VGS_{I3 \mu n}^{I}$ |
| Spectra $I_4$ | ... | ... |
| ... | ... | ... |

STEP 1
Obtain spectral analyses of
product E using spectrometer I
to determine characteristics

STEP 2
Obtain and/or record spectral couples of
Product i obtained from spectrometers I and II
Spectra SIIi is at least one product i measured from spectrometer II
Spectra SIi is at least one product i measured from spectrometer I

STEP 3
Measure spectrum of product X by spectrometer II

STEP 4
Determine function to correlate spectrum of product X
with spectra SIIi using method of analysis by proximity

STEP 5
In function of step 4, replace values of spectral quantities SIIi
by values of corresponding spectral quantities SIi of the
spectral couples to determine a spectrum SIx

STEP 6
Applying model of step (1) to spectrum SIx
to determine and/or predict characteristics of product X

US 9,915,606 B2

METHOD FOR TRANSFERRING BETWEEN SPECTROMETERS

CROSS-REFERENCE TO RELATED APPLICATIONS

This application is the United States National Phase of PCT Application No. PCT/EP2014/064808 filed 10 Jul. 2014, which claims priority to European Patent Application No. 13290161.2 filed 12 Jul. 2013, each of which is incorporated herein by reference.

The present invention relates to a method for characterizing a sample product X by spectral analysis by means of a new spectrometer II using information acquired by means of a first spectrometer I. The invention further concerns a method for transferring knowledge acquired by means of a first spectrometer I, in order to use a new spectrometer II in a novel and more efficient manner.

It is known to develop calibration functions for transferring between spectrometers. For example, in M. Forina "Transfer of calibration function in near-infrared spectroscopy", in "Chemometrics and Intelligent Laboratory Systems, Volume 27 Issue 2, February 1995, pages 189-203, a method is described for transferring the regression equation in near-infrared spectroscopy (NIR spectroscopy) from a first instrument to a second instrument. The method employs twice iterated regressions by means of the partial least squares method (PLS)—in the first step to calculate the ratio between the spectra of the two samples, and in the second step to calculate the regression equation (relationship between the variables and the chemical spectral variables) of the first instrument. The two PLS steps are combined in order to predict the regression equation for the second instrument.

This type of methodology developed in the prior art is very cumbersome and not necessarily suited to particular situations such as the transfer of knowledge acquired by means of a first spectrometer (e.g. a laboratory spectrometer coupled to an important non-transportable computer) to a new spectrometer (for example, a portable spectrometer and/or a spectrometer coupled to a portable computer and/or an online installation).

Another drawback connected to the prior art methods lies in the need to establish a new spectral data databank for the new spectrometer, from a substantial initial number of standardizing samples—in the prior art one finds mention of basic databases derived from at least 60 or 100 standardizing samples. In most of the examples, even larger databanks of data from standardizing samples are described, because the mathematical regression methods underlying the databanks often require hundreds or even thousands of standardizing samples. The present invention allows one to overcome this previous requirement, which opens up a large number of new applications, as demonstrated below.

The Applicant has developed a novel, effective, and efficient method that has been found to be much simpler to implement than the techniques according to the prior art. This novel method and its advantages will be described in detail in the following description and in the examples, figures and claims. Other objects and advantages of the present invention will become apparent from the following description relating to embodiments which are only offered as indicative examples and do not limit the scope of the invention.

This description may be better comprehended with reference to the accompanying FIGS. 1-3, wherein:

FIG. 2 illustrates a databank for spectral data and for characterization.

According to one embodiment, the present invention comprises a method of determining and/or predicting a characteristic, CAR, of a sample product x, by spectral analysis by means of a new spectrometer II,
which method is characterized in that:
1. spectral analyses are performed on standardizing sample products E by means of a first spectrometer I for which there is at least one model enabling one to determine and/or predict the aforesaid characteristic, CAR, from said standardizing sample products E (and optionally the products i below) and from their spectrum obtained by means of said first spectrometer I;
2. spectral couples of products i obtained from the first spectrometer I and the new spectrometer II, respectively (SIi and SIIi) are obtained and/or are recorded;
3. by means of the new spectrometer II, the spectrum of the sample product x (spectrum SIIx) is measured;
4. the distance(s) between the spectrum of the sample product x (SIIx) and the spectrum (spectra) SIIi of the said product(s) i are determined;
5. the distance(s) determined in the preceding step is (are) taken into account in deducing an equivalent distance from the spectra SIi which allow one to determine an SIx and a model according to step (1) supra; and
6. in this manner, one determines and/or predicts the characteristic, CAR, of the sample product x being studied.

According to a preferred embodiment, the present invention also comprises a method of determining and/or predicting a characteristic, CAR, of a sample product x, by spectral analysis by means of a new spectrometer II,
which method is characterized in that:
1. spectral analyses are performed on sample products E by means of a first spectrometer I for which there is at least one model enabling one to determine and/or predict the aforesaid characteristic, CAR, from said standard products E (and optionally the products i below) and from their spectrum obtained by means of said first spectrometer I;
2. spectral couples of products i obtained from the first spectrometer I and the new spectrometer II, respectively (SIi and SIIi) are obtained and/or are recorded;
3. by means of the new spectrometer II, the spectrum of the sample product x (spectrum SIIx) is measured;
4. the function enabling one to correlate the spectrum of the sample product x (SIIx) with the spectra SIIi is determined by means of a method of analysis by proximity;
5. in the said function, one replaces the values of spectral quantities SIIi by values of corresponding spectral quantities SIi of the spectral couples, thereby determining a spectrum SIx; and
6. the model of step (1) supra is applied to the spectrum SIx in such a manner as to determine and/or predict the characteristic, CAR, of the sample product x being studied.

In the form of this preferred embodiment, the present invention comprises transforming the spectrum SIIx obtained by means of the new spectrometer II into a spectrum SIx which can be employed by means of the model(s) already available for the first spectrometer I.

This novel methodology enables one to optimize and facilitate the implementation of new spectrometers while taking advantage of knowledge previously acquired from other spectrometers, and without employing the very cumbersome mathematical regression techniques employed in the prior art.

Figure 1:
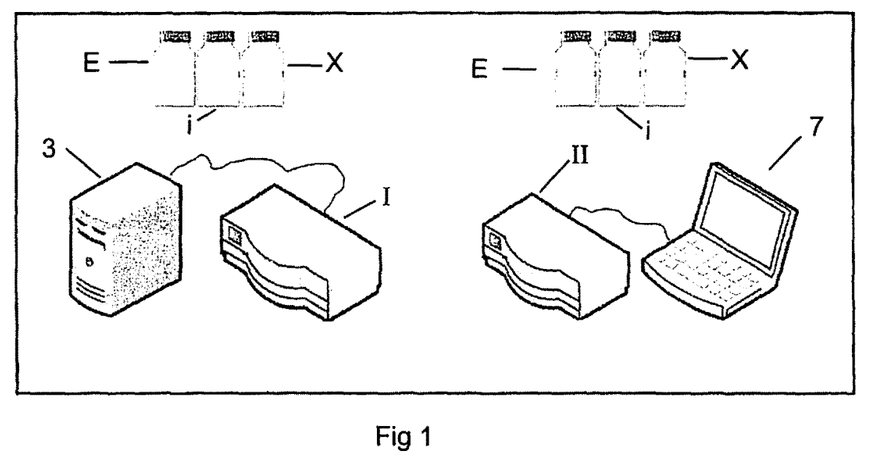
FIG. 1 is a schematic representation of instruments which can benefit from the advantages of the inventive method.

FIG. 1 is a schematic representation of instruments which can benefit from advantages of the method according to the present invention. A first spectrometer I is shown which is coupled to a central computer unit 3, and a second spectrometer II is shown which is coupled to a portable computer 7 and/or an online installation.

One appreciable advantage of the method according to the present invention compared to techniques developed in the prior art is that it is unnecessary to provide new correlation functions between the characteristics of the new product and its spectrum SIIx. Instead, one makes use of the knowledge previously acquired on a different spectrometer.

A second appreciable advantage of the method according to the invention compared to techniques developed in the prior art is that it is sufficient to have a limited number of spectra of products i obtained by means of the new spectrometer II and by means of the spectrometer I. This limited number of "spectral couples" of products i (SIIi and SIi) is generally dictated by the customer and/or by the ultimate user, who desire(s) to use methods of control which are reactive and reliable while limiting the need to initially provide a large number of standards (standardizing samples).

A characteristic of the method according to the present invention is that it enables one to avoid the requirement of a large number of standardizing samples experienced with the prior art. For example, the present invention allows one to characterize a product sample from a number of spectral couples of products i which is less than 100, or less than 60, or even less than 50, for example. Significant results have been obtained using the present invention based on less than 40 or 30, or even, e.g., less than 20 spectral couples. A minimum of 5 spectral couples of products i (SIi and SIIi) is preferred, although the present invention has been used successfully with a minimum of 3 spectral pairs of products i (SIi and SIIi) available.

The present invention may advantageously be applied to all types of spectroscopy, e.g. (the examples given being non-limitative): Raman spectroscopy, infrared spectroscopy, near-infrared spectroscopy (NIR spectroscopy), and visible and UV spectroscopy. The present invention is preferably applied to NIR spectroscopy. NIR spectroscopy has associated with it various advantages compared to other analytical methods, e.g. in refineries, or petrochemical or chemical installations, and in situations where one seeks to characterize chemical products, e.g. hydrocarbons, particularly fuels, where it is desired to execute a large number of repetitive analyses ("applications") accurately, rapidly, and online. Furthermore, most molecular information in the form of combinations of polyatomic vibrations, and harmonics of these, are present in the NIR region between 800 and 2500 nm.

The method according to the present invention is particularly well adapted to characterization of a product by topological spectral analysis in the near-infrared region (NIR).

The characterization of a product according to the invention may consist of determination and/or prediction of any chemical, physical, or physicochemical characteristic of the product, and/or identification of a type and/or family of products.

The method according to the present invention thus consists of a step characterized in that one provides spectral analyses carried out on standardizing sample products E by means of a first spectrometer I for which at least one model exists which enables one to determine and/or predict a characteristic CAR from the said standardizing sample products E and from their spectra obtained by means of said first spectrometer I.

For illustrative purposes (but not limitative), this step may thus be characterized by establishment of a databank of spectral data such as described in the patent EP0742900, preferably an augmented databank of spectral data such as described in Eur. Pat. App. 1329099.4 filed on 30 Apr. 2013 by the present Applicant.

A graphic representation of the databank of spectral data, in the form of a table, is provided for illustrative purposes in the accompanying FIG. 2. This table comprises a truncated view of the databank (in reality, the databank comprises numerous columns representing the wavelengths and/or ranges of wavelengths (or, equivalently, wave numbers or ranges of wave numbers) extracted from corresponding spectra). According to one embodiment of the present invention, the number of wavelengths chosen may be from 2 to 2000, e.g. from 3 to 1000, from 5 to 200, or from 40 to 80.

The wavelengths chosen may be at regular intervals, such as 1 to 50 nm, or 10 to 50 nm, or 15 to 35 nm, or 1 to 5 nm, or 1 nm; or they may be at irregular intervals, e.g. 1 to 200 nm, 1 to 100 nm, or 1 to 50 nm, particularly 2 to 50 nm, or 4 to 50 nm, or 10 to 60 nm, which may be specifically chosen, or may be aleatory based on the form of the spectral curve at the given wavelength, e.g. a peak, a valley, or a shoulder, or they may be chosen based on chemical characteristics, or statistical characteristics such as factorial analysis. The wavelengths may be in the range 600 to 20,000 nm, e.g. 625 to 2600 nm, or 800 to 2600 nm, or particularly 1500 to 2600 nm or 2000 to 2500 nm. The wave numbers may be in the range 16,600 to 500 $cm^{-1}$, for example 16,000 to 3840 $cm^{-1}$, or 12,500 to 3840 $cm^{-1}$, particularly 6660 to 3840 $cm^{-1}$, or 5000 to 3900 $cm^{-1}$; the corresponding frequencies in Hertz may be obtained by multiplying the wavelengths by $3 \times 10^{10}$ cm/sec.

Before being able to determine and/or predict a characteristic CAR of a sample, it is clear that one must measure the values of the property for a sufficient number of standardizing sample products E. Thus, according to an embodiment of the present invention, the chemical, physical, and/or physicochemical properties of standardizing sample products E are determined by means of conventional techniques of analysis. As an example (non-limitative) of conventional techniques of analysis, one might mention chromatography in the gas phase for chemical compositions. Although it goes without saying that the standardizing samples are selected to cover the range in which the method is to be used, in a preferred embodiment the present invention provides for working with a limited number of standards through the methodology of expansion of the aforementioned spectral databank, as described in Eur. Pat. App. 1329099.4 filed 30 Apr. 2013 by the present Applicant, which is incorporated herein by reference.

Thus, according to the present invention, one adds to the spectral database the values of desired properties measured for the described standardizing samples. This leads to a spectral database consisting of a number of points which are associated with the desired properties. An exemplary embodiment (truncated view) is presented in FIG. 2.

This is an illustration of an expanded spectral database E consisting of standardizing samples (A) and intergerms (IG) as defined in the European patent application 1329099.4. The table has been supplemented by the characteristics of the desired target products, which in this example are the RON and MON values (the research octane number RON and the motor octane number MON). These characteristics were therefore measured for the standardizing samples and calculated for the intergerms.

For the purpose of describing at least one embodiment of obtaining and utilizing the model whereby it is possible, starting with a new spectrum plus spectra of standardizing sample products E, to determine and/or predict a characteristic or property of a product, we will rely on the description that is provided in the patent EP07422900, which is incorporated herein by reference. In the Specification in EP0742900, the signals, e.g. the absorptions (or their derivatives) of the new spectrum, are compared with signals, e.g. absorptions (or their derivatives) at the same wavelength of standardizing sample products E, and the standardizing samples having the smallest differences are selected. Then the properties of these chosen standardizing samples are averaged in order to determine the characteristic or property of the unknown sample.

According to a preferred method according to the present invention, this comparison of signals is not carried out for the entirety of the databank of spectral data but only for the part of the databank of spectral data which is representative of a homogeneous sub-group which preferably represents the property or characteristic which is sought; this method of discrimination is described in particular in Eur. Pat. App. 1329099.4, which is incorporated herein by reference.

Then the signals, e.g. the absorptions (or their derivatives, or some other quantity associated with the spectrum) of the new spectrum are compared with the same signals at the same wavelength, of the standardizing samples in the same homogeneous group or sub-group, and the standardizing samples having the smallest difference are selected from the spectral database.

Whatever the method used, hereinafter we will refer to the close points of the new spectrum as the "close neighbors". Then, e.g., one can average the properties of these standardizing samples to determine the desired characteristic or property of the sample corresponding to the new spectrum.

In a particular method according to the present invention, the "close neighbors" chosen are those with the smallest average absolute values of the difference at each wavelength i between the spectral quantity (represented for example by absorbance or a derivative thereof), Wix, for the target product (e.g. a sample corresponding to the new spectrum) and the corresponding signal, Wim, for the "close neighbor". The averages may relate for example to the average value of (Wix minus Wim) (whatever the sign of that value, i.e. the absolute value of the difference), or to the square of (Wix minus Wim). For each "close neighbor" in the spectral database for the type of product in question, the average difference as described is found, and the "close neighbor" having the smallest average differences is chosen, namely at least one but preferably two (or as many as 1000 smallest, for example 2 to 100 or 2 to 20 smallest, but particularly 2 to 10 and especially 2 to 6 smallest). This selection of the "close neighbors" can be accomplished by any known method, e.g. the methods described in the Specification of the patent EP0742900 may be used (e.g. with determination of the "proximity index"). According to a particular embodiment of the present invention, the number of close neighbors may be equal to 1, preferably greater than or equal to 2, more preferably greater than or equal to 3. According to an embodiment of the present invention, the number of "close neighbors" is less than or equal to 50, for example less than or equal to 20, or in particular less than or equal to 10.

As indicated above, from the time that one selects the "close neighbor" points, one can easily average the properties of these selected "close neighbors" in order to determine the property of a sample which sample corresponds to a new spectrum.

However (and this constitutes a preferred embodiment of the present invention), the Applicant has discovered (as described in Eur. Pat. App. 13290098.6, filed 30 Apr. 2013, which is incorporated herein by reference) that a significant improvement in the accuracy and robustness of the Applicant's method in determination of the desired characteristic (e.g. a property) of a product corresponding to a new spectrum is achieved by carrying out a weighted average of the properties of the described "close neighbor" points (whether standardizing and/or "intergerms" and/or "extragerms" and/or "poles", said weighting being a linear or nonlinear function which is inversely proportional to the distance between the sample (the "target product") and the "close neighbor" points selected.

Thus, according to the present invention, one has spectral analyses obtained on standardizing sample products E by means of a first spectrometer I, for which there exists at least one model allowing one to determine or predict the characteristic CAR, from these standardizing sample products E, and from their spectra obtained by means of the first spectrometer I.

Figure 3:
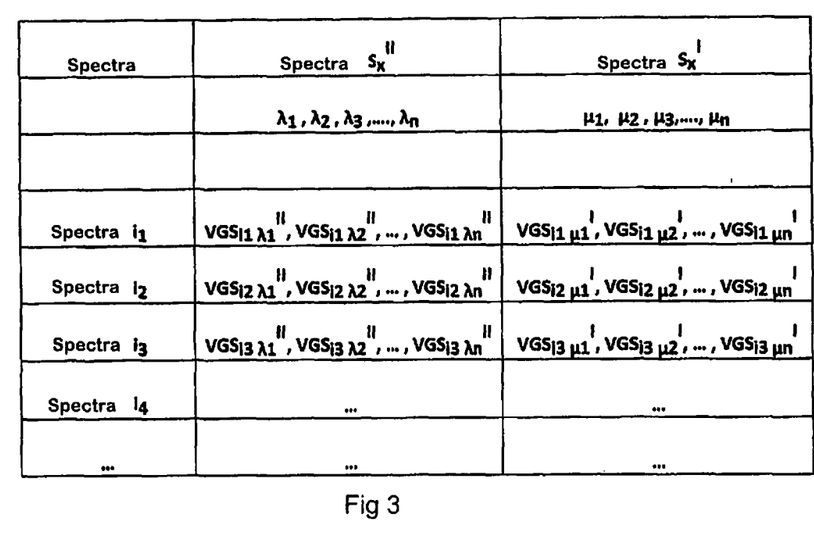
FIG. 3 illustrates the spectral couples according to the present invention.
Figure 4:
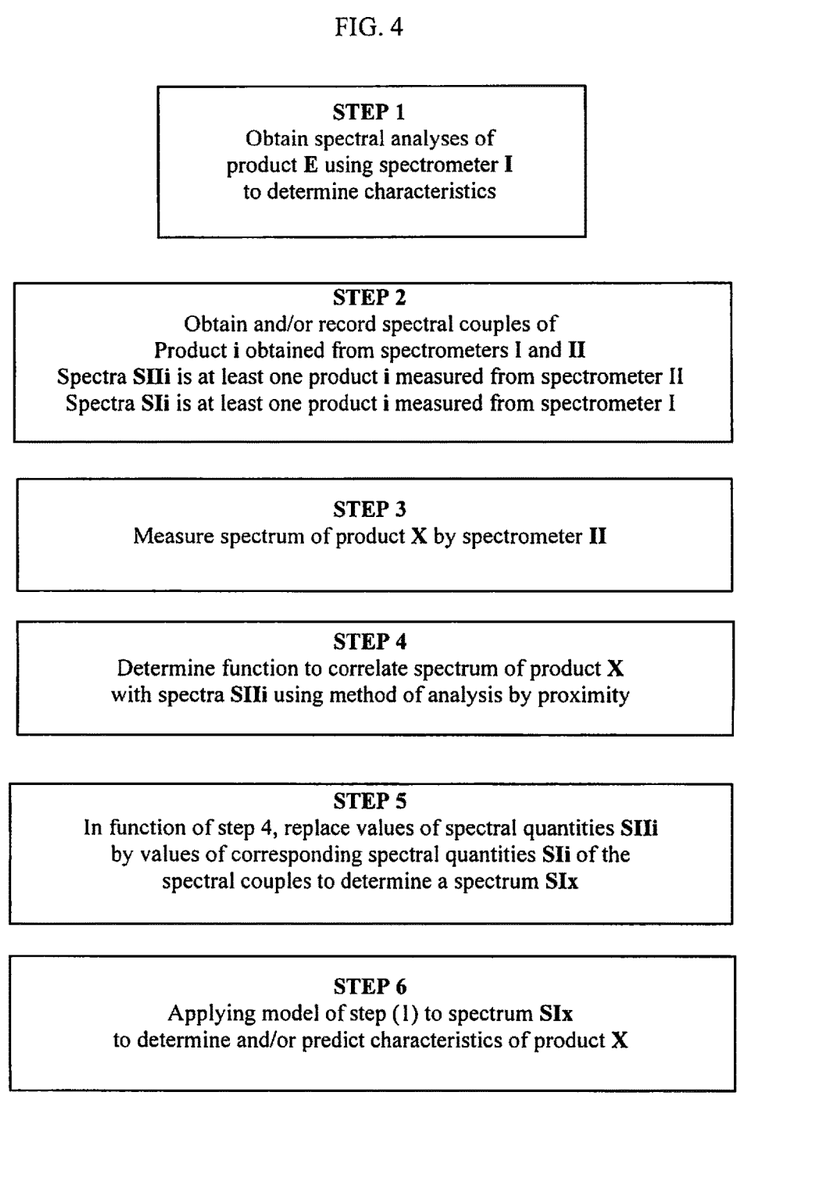
FIG. 4 is a block diagram of a method according to the present invention.

The method according to the present invention therefore comprises also a step characterized in that one obtains and/or records spectral couples of products i obtained by the first spectrometer I and by the new spectrometer II, respectively (SIi and SIIi). The spectra SIIi are the spectra of products i measured using the new spectrometer II, and the spectra SIi are the spectra of products i measured using the spectrometer I. According to an embodiment according to the present invention, from these spectra SIIi and SIi one constructs a table, an exemplary representation of which is presented in FIG. 3, for purposes of illustration (non-limitative). From the table shown in FIG. 3 one can see:
- in the first column: references which allow one to identify the names of the spectra of the products i;
- in the second column, second line: values of wavelengths (and/or ranges of wavelengths) (or, equivalently, wave numbers or ranges of wave numbers) established from the new spectrometer II;
- in the second column, starting with the third line: the values (VGS) of the spectral quantities (e.g. absorption, or a derivative of the absorption, or some other value which is representative of the spectral quantity) corresponding to couples consisting of the reference product i and the wavelength, established from the new spectrometer II;
- in the third column, second line: values of the wavelengths (and/or ranges of wavelengths) (or, equivalently, wave numbers or ranges of wave numbers) established from the first spectrometer I;
- in the third column, starting with the third line: the values (VGS) of the spectral quantities (e.g. absorption, or a derivative of the absorption, or some other value which is representative of the spectral quantity) corresponding to couples consisting of the reference product i and the wavelength, established from the first spectrometer I.

The spectral quantities may thus be any type of signals which characterize the spectra, e.g. absorbance, transmittance, reflectance, etc.; the most commonly used signals are absorbances or optical densities. One might also mention, as an example of signals, derivatives of absorbances, or any other measurement resulting from another type of mathematical treatment of such absorbances (e.g. Fourier transforms).

The method according to the present invention thus also comprises an additional step characterized in that the spectrum of the sample product x (spectrum SIIx) is measured by means of the new spectrometer II. This measurement is carried out in exactly the same manner as the measurement carried out in the preceding step in the new spectrometer. Regarding the said new spectrometer, all that is available at this stage are spectra II (SII) of the products i and of the sample product x.

Although this does not constitute a preferred embodiment of the present invention, at this stage one may also measure the characteristic or property of the products i, and integrate them into the spectral database of the first step; this would thus enable one to integrate the data for these products i into the model. However, and this does constitute a preferred embodiment of the present invention, it is possible not to measure any characteristic or property of the products i; thus in the present invention one is limited to the spectral measurements as described above.

The method according to the present invention thus comprises an additional step, characterized in that one determines the distance(s) between the spectrum of the sample product x (SIIx) and the spectrum (or spectra) of the aforesaid product(s) i. According to a preferred embodiment, the distance may advantageously be determined by a method of analysis by closeness, which enables one to establish a function which correlates the spectrum of the sample product x (SIIx) with the spectrum (or spectra) SIIi. The measurement of the distance may be carried out with regard to all of the spectra of the products i; however (and this represents a preferred embodiment of the present invention), the measurement of the distance is carried out only with regard to the spectra of products i which are considered to be "close neighbors" in the information accumulated from the new spectrometer II (the points i of the sample product x which are close). According to a particular embodiment of the present invention, the number of "close neighbors" may be equal to 1, preferably greater than or equal to 2, particularly preferably greater than or equal to 3. Considering that the object of the present invention is to enable rapid use and rapid calibration of a new spectrometer by carrying out a limited number of spectral analyses on the new spectrometer, the number of "close neighbors" will be less than or equal to the total number of products i (as described above), and preferably less than or equal to half of the total number of products i.

The method according to the present invention thus comprises two additional steps, characterized in that:
one takes into account the distance(s) determined in the preceding step, and from the model according to item (1) above; and
thereby one determines and/or predicts the desired characteristic CAR of the sample product x.

According to a preferred embodiment, these two additional steps consist of
replacing the values of the spectral quantities SIIi in the function of the preceding step by corresponding values of spectral quantities SIi of the spectral couples, to thereby determine a spectrum SIx; and
applying the model of item (1) above to the spectrum SIx, to determine and/or predict the desired characteristic, CAR, of the sample product x.

There is no critical requirement regarding selection of the standardizing sample products E and/or of the products i.

However, such standardizing sample products E and/or such products i preferably represent all the families of products that may be analyzed by the spectrometer I and/or the spectrometer II. They can therefore be selected from the aforementioned families of products that may be analyzed by the spectrometer I and/or the spectrometer II; and/or from components (e.g. pure products) of said products; and/or from combinations of said components.

It is also evident that the choice and/or selection of the described standardizing sample products E and/or of the products i may evolve over time as new types of families of products susceptible to be analyzed by spectrometer I and/or spectrometer II become available.

As an example, the products i will be selected such that the cover the maxima in the pertinent spectral envelopes; they may comprise, e.g., a spectral subset of the standardizing sample products E and/or of the sample products x.

Thus, the characterization of a product according to the present invention may consist of a determination and/or prediction of any chemical, physical, or physicochemical characteristic of the product, and/or the identification of a type and/or family of products.

For example, one may determine the presence of individual chemical compounds in a composition, and their concentrations; one may also determine any type of property. Examples of such properties are provided below.

Thus, the method may be employed for the determination of product characteristics from the food industry, e.g. characteristics of water, alcohols, lotions, or oils, especially olive oil.

The method may also be advantageously employed for physicochemical determination or prediction regarding at least one feedstock or a regarding a product used in a petroleum refining industrial process and/or in petrochemical operations, or a product obtained in the use of such processes or operations. Such a process may be a hydrocarbon conversion or separation process, preferably a process of reforming or catalytic cracking or hydrotreatment, or distillation or blending. In particular, the method may be used for determining at least one property of a feedstock and/or for predicting and/or determining at least one property and/or a yield of a product from a number of different processes, such as processes for separating petroleum products, e.g. atmospheric distillation, vacuum distillation, distillation at a pressure higher than atmospheric pressure, or processes of thermal or catalytic conversion, with or without partial or complete hydrogenation, of a petroleum product, such as catalytic cracking, e.g. fluid catalytic cracking (FCC), hydrocracking, reforming, isomerization, selective hydrogenation, or alkylation.

Use of the method in blending operations implies prediction and/or determination of at least one property of a mixture of liquid hydrocarbons (possibly with other additives such as alkyl ethers), and such use is particularly valuable; the method may or may not comprise determination, for each constituent of the blend, a "blending index" for the property in question. In this method as applied to a blend, one may obtain the "blending indices" simply by calculation and without the need to actually prepare physical mixtures of samples, other than those contained in the database. One may linearly or nonlinearly combine the "blending indices" in the domains of stability, to determine, from the value of this combination, a value for at least one property of the blend obtained. One may realize the blend by mixing at least two components from among butane, "vapocracked hydrogenated essence", the isomerate, the reformate, MTBE or TAME, and the essence derived from the FCC. One may repeat this process by numerically adding the other constituents separately to the liquid hydrocarbon base, in order to determine a series of "blending indices" and then to determine, from these indices, the properties of the multi-constituent blend.

Examples of properties which one may determine and/or predict are the following: for automotive fuels and essences, at least one from among the research octane number (RON), motor octane number (MON), and/or the arithmetic average of these, with or without lead as an additive; and or the content of methyl t-butyl ether or methyl isoamyl ether, and/or of benzene.

For automotive fuels and essences, relevant properties may be at least one from among: vapor pressure, density (mass per unit volume), volatility, distillation curve characteristics (e.g. percentage distilled up to 70° C. and/or up to 100° C.), oxygen content, benzene content, or sulfur content, chemical composition and/or gum content (e.g. expressed as mg per 100 mL), and/or the sensitivity to lead; these properties may be determined in particular for use in operations of blending.

For the fuels diesel oil and gas oil, relevant properties may be at least one from among: the cetane number (e.g. measurement at the motor level), the calculated cetane number, the cloud point, the "discharge point", the filterability, the distillation curve, the mass per unit volume (e.g. at 15° C.), the flash point, the viscosity (e.g. at 40° C.), the chemical composition, the sensitivity to additives, and the percentage of sulfur.

For distillation products from crude petroleum, e.g. under atmospheric pressure, the relevant properties may be at least one from among: the mass per unit volume, the percentage of sulfur, the viscosity at 100° C., the distillation curve, the content of paraffins, the residual carbon content or the Conradson carbon content, the content of naphtha, the flash point of the oil, the cloud point for the gas oil (e.g. light gas oil), and/or the viscosity at 100° C., and/or the sulfur content for atmospheric residues, the yield of at least one of the cuts, [e.g.] essence (boiling range 38-95° C.), benzene cut (boiling range 95-149° C.), naphtha cut (boiling range 149-175° C.), kerosene cu (boiling range 175-232° C.), light gas oil cut (boiling range 232-342° C.), heavy gas oil cut (boiling range 342-369° C.), and the atmospheric residue above 369° C.

For at least one from among a feedstock or a product of a catalytic cracking process, e.g. an FCC process, the relevant properties may be at least one from among: the mass per unit volume, the percentage of sulfur, the aniline point, the gas oil number, the essence number, the viscosity at 100° C., the index of refraction at 20 and/or 60° C., the molecular weight, the distillation temperature (e.g. the distillation temperature for 50% distillation), the percentage of aromatic carbon, the total content of nitrogen, and factors characterizing the susceptibility of the feedstock to cracking, e.g. the KUOP, the crackability factor, the cokeability factor, and the yield of, e.g., gas, essence, gas oil, or residue. Thus, one may determine the yields and/or the properties of various products obtained by distillation of cracked products, such as the RON and/or the MON, without an octane enhancing additive or lead additives, for the essence cut, and the viscosity at 100° C. for the distillation residue.

For at least one from among a product or a feedstock of a catalytic reforming process, the relevant properties may be at least one from among: the mass per unit volume, the distillation temperature, the RON (and/or MON), the vapor pressure of the essence cut without an octane enhancing additive or lead additive, the volatility, the chemical composition (expressed in percentages), namely the composition in terms of linear saturated hydrocarbons, isoparaffins, naphthenes, aromatic substances (e.g. benzene and mono- and disubstituted benzenes), olefins (e.g. cyclic and non-cyclic olefins), and diolefins, and the maleic anhydride index.

For at least one from among a product or a feedstock of a process of hydrogenation of an essence cut, the relevant properties may be at least one from among: the mass per unit volume, the distillation temperature, the RON (and/or MON), the vapor pressure of the essence cut without an octane enhancing additive or lead additive, the volatility, the chemical composition (expressed in percentages), namely the composition in terms of linear saturated hydrocarbons, isoparaffins, naphthenes, aromatic substances (e.g. benzene and mono- and disubstituted benzenes), olefins (e.g. cyclic and non-cyclic olefins), and diolefins, and the maleic anhydride index.

The invention claimed is:

1. A method of determining, predicting, or both determining and predicting a characteristic, CAR, of a sample product x, by spectral analysis by means of a new spectrometer II, said method comprising the steps of:
   (1) performing spectral analyses on standardized-sample products E by means of a first spectrometer I for which there is at least one model to determine and/or predict the characteristic, CAR, from said standardized-sample products E and from the spectrum obtained by means of said first spectrometer I;
   (2) performing, recording or both performing and recording spectral couples consisting of at least one of a number of products i and at least one wavelength obtained from the first spectrometer I and the new spectrometer II, a spectra SIIi being the spectra of at least one of a number of products i measured using the new spectrometer II and a spectra SIi being the spectra of at least one of a number of product i measured using the spectrometer I;
   (3) measuring by means of the new spectrometer II, the spectrum of the sample product x (spectrum SIIx);
   (4) determining a function to correlate the spectrum of the sample product x (SIIx) with the spectra SIIi by means of a method of analysis by proximity;
   (5) in the function, replacing values of spectral quantities SIIi by values of corresponding spectral quantities SIi of the spectral couples, thereby determining a spectrum SIx; and
   (6) applying the model of step (1) to the spectrum SIx to determine, predict or both determine and predict the characteristic, CAR, of the sample product x being studied.

2. A method according to claim 1 wherein the number of spectral couples of at least one product i (SIi, SIIi) available is selected from the group consisting of less than 100, 60, or 50.

3. A method according to claim 1 wherein step (4) is carried out on a number of products i less than or equal to one half the total number of products i available from step (2).

* * * * *